(12) United States Patent
Paulus

(10) Patent No.: US 9,700,366 B2
(45) Date of Patent: Jul. 11, 2017

(54) POLYPHASE ELECTROSURGICAL SYSTEM AND METHOD

(75) Inventor: Joseph A. Paulus, Louisville, CO (US)

(73) Assignee: COVIDIEN LP, Mansfield, MA (US)

( * ) Notice: Subject to any disclaimer, the term of this patent is extended or adjusted under 35 U.S.C. 154(b) by 1645 days.

(21) Appl. No.: 12/184,556

(22) Filed: Aug. 1, 2008

(65) Prior Publication Data

US 2010/0030210 A1 Feb. 4, 2010

(51) Int. Cl.
*A61B 18/12* (2006.01)
*A61B 18/00* (2006.01)
*A61B 18/14* (2006.01)

(52) U.S. Cl.
CPC .. *A61B 18/1206* (2013.01); *A61B 2018/0075* (2013.01); *A61B 2018/00654* (2013.01); *A61B 2018/00684* (2013.01); *A61B 2018/00732* (2013.01); *A61B 2018/00875* (2013.01); *A61B 2018/128* (2013.01); *A61B 2018/143* (2013.01)

(58) Field of Classification Search
CPC .. A61B 2018/0075; A61B 2018/00654; A61B 2018/128; A61B 2018/1467
USPC .......... 606/33–34; 600/393; 607/98, 99, 102
See application file for complete search history.

(56) References Cited

U.S. PATENT DOCUMENTS

| | | | |
|---|---|---|---|
| 2,331,247 A | 10/1943 | Symons | |
| 3,514,689 A | 5/1970 | Giannamore | |
| 3,697,808 A | 10/1972 | Lee | |
| 3,766,434 A | 10/1973 | Sherman | |
| 4,415,763 A | 11/1983 | Cookson | |
| 4,532,924 A | 8/1985 | Auth et al. | |
| 4,572,190 A | 2/1986 | Azam et al. | |
| 4,630,218 A | 12/1986 | Hurley | |
| 4,672,980 A | 6/1987 | Turner | |
| 4,785,829 A | 11/1988 | Convert et al. | |
| 5,220,927 A | 6/1993 | Astrahan et al. | |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

European Search Report for EP 2 149 342 dated Dec. 8, 2009. (5 pages).

(Continued)

*Primary Examiner* — Thomas Giuliani

(57) ABSTRACT

A polyphase electrosurgical system and method are provided. In embodiments, a radiofrequency generator having the capability of delivering a plurality of independent electrosurgical signals is disclosed. An electrosurgical instrument having an array of electrodes that correspond to the plurality of signals may be used to deliver the electrosurgical signals to tissue. In embodiments, three RF signals having a phase offset of about 120° therebetween, i.e., a three-phase configuration, may be used to achieve a balanced delivery of electrosurgical energy, which may lead to increased rates of energy delivery, improved control of tissue ablation regions, and improved operative outcomes. The phase, amplitude, and/or frequency of each signal may be independently variable in response to user inputs and/or biological parameters such as tissue impedance or return electrode current.

17 Claims, 6 Drawing Sheets

(56) References Cited

U.S. PATENT DOCUMENTS

| | | | |
|---|---|---|---|
| 5,354,325 A | | 10/1994 | Chive et al. |
| 5,383,917 A | * | 1/1995 | Desai .................. A61B 18/12 606/31 |
| 5,542,916 A | * | 8/1996 | Hirsch ................. A61B 18/00 604/164.08 |
| 5,602,812 A | * | 2/1997 | Miura .................. G11B 20/10 369/47.3 |
| 5,620,481 A | | 4/1997 | Desai et al. |
| 6,059,778 A | | 5/2000 | Sherman |
| 6,200,314 B1 | | 3/2001 | Sherman |
| 6,238,387 B1 | * | 5/2001 | Miller, III .......... A61B 18/1206 606/34 |
| 6,488,678 B2 | | 12/2002 | Sherman |
| 6,794,929 B2 | | 9/2004 | Pelly |
| 7,145,757 B2 | | 12/2006 | Shea et al. |
| 7,151,964 B2 | | 12/2006 | Desai et al. |
| 2003/0069619 A1 | * | 4/2003 | Fenn et al. .................... 607/101 |
| 2003/0195501 A1 | * | 10/2003 | Sherman ............ A61B 18/1206 606/34 |
| 2005/0043726 A1 | * | 2/2005 | McHale ............ A61B 17/22004 606/27 |
| 2006/0015095 A1 | | 1/2006 | Desinger et al. |
| 2007/0088413 A1 | * | 4/2007 | Weber ................... A61B 18/14 607/99 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 1366724 B1 | 11/1996 |
| EP | 0833592 B1 | 4/1998 |
| EP | 836868 | 4/1998 |
| EP | 1051948 | 11/2000 |
| EP | 1465037 | 10/2004 |
| EP | 880220 | 6/2006 |
| EP | 1707144 | 10/2006 |
| EP | 2149342 | 7/2009 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2 331 247 | 5/1999 |
| GB | 2358934 | 8/2001 |
| JP | H08299356 A | 11/1996 |
| JP | 2004160084 A | 6/2004 |
| SU | 166452 | 1/1965 |
| SU | 727201 | 4/1980 |
| WO | 95/25472 | 9/1995 |
| WO | WO 96/39088 | 12/1996 |
| WO | 98/07378 A1 | 2/1998 |
| WO | WO 99/56647 | 11/1999 |

OTHER PUBLICATIONS

U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.

(56) References Cited

OTHER PUBLICATIONS

Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
EP Exam Report from Appl. No. 09 009 860.9 dated Sep. 6, 2016.

* cited by examiner

POLYPHASE ELECTROSURGICAL SYSTEM AND METHOD

BACKGROUND

1. Technical Field

The present disclosure relates to electrosurgical instruments for open, percutaneous, endoscopic, or laparoscopic surgical procedures. More particularly, the present disclosure relates to a radiofrequency tissue ablation system having multiple, independently-phased electrodes for providing rapid energy delivery and improved ablation control.

2. Background of Related Art

The use of electrical energy including radiofrequency and microwave energy and, in particular, radiofrequency ("RF") electrodes or microwave antennae for ablation of tissue in the body or for the treatment of pain is known. Generally, RF electrodes (e.g., probes, resistive heating elements, and the like) include an elongated cylindrical configuration for insertion into the body to target tissue that is to be treated or ablated. The RF electrodes can further include an exposed conductive tip portion and an insulated portion. The RF electrodes can also include a method of internal cooling, such as the RF electrodes shown and described in U.S. Pat. No. 6,506,189 entitled "COOL-TIP ELECTRODE THERMOSURGERY SYSTEM" issued to Rittman, III et al., on Jan. 14, 2003 and U.S. Pat. No. 6,530,922 entitled "CLUSTER ABLATION ELECTRODE SYSTEM" issued to Cosman et al., on Mar. 11, 2003. Accordingly, when the RF electrode is connected to an external source of radiofrequency power, e.g., an electrosurgical generator (device used to generate therapeutic energy such as radiofrequency, microwave, or ultrasonic), and current is delivered to the RF electrode, heating of tissue occurs near and around the exposed conductive tip portion thereof, whereby therapeutic changes in the target tissue, near the conductive tip, are created by the elevation of temperature of the tissue.

In some applications, for example, tumor ablation procedures, multiple electrodes may be inserted into the body in an array to enlarge ablation volumes. In a particular application, arrays of high frequency electrodes are inserted into tumors. The electrodes are typically placed in a dispersed fashion throughout the tumor volume to cover the tumor volume with uniform heat. In one common arrangement, the electrodes are arranged in a delta (i.e., triangular) configuration. The multiple electrodes may be activated simultaneously or sequentially with high frequency energy so that each electrode heats the surrounding tissue. Simultaneous activation allows maximum energy to be applied to the tissue, but may also have drawbacks. Current from the electrodes tends to travel away from the electrode array, causing an isopotential area or volume, (i.e., a dead zone), to form between the electrodes. Such an isopotential area may result in incomplete ablation of targeted tissue because insufficient energy is delivered to the isopotential region. Series activation, wherein energy is applied to fewer than all electrodes at a time (typically one or two electrodes at a time) can prevent the formation of an isopotential region between the electrodes. However, the sequence of cycling energy through the electrodes in this manner may also have drawbacks, because it limits the rate of energy delivery into tissue.

SUMMARY

The present disclosure provides a system and method for supplying energy to multiple electrodes in an electrode cluster, while minimizing or eliminating the isopotential area or volumes enclosed by the electrode cluster.

In an embodiment in accordance with the present disclosure, a polyphase RF generator having the capability of generating a plurality of independent RF signals is provided. The phase, amplitude, and/or frequency of each RF signal may be independently variable. The RF signals may be characterized by a substantially sinusoidal waveform, or may alternatively exhibit non-sinusoidal characteristics. Each independent signal may be operably coupled to a corresponding electrode of the surgical instrument. The independent RF signals may be concurrently generated.

In an embodiment, a polyphase RE generator according to the present disclosure may be configured to generate three RF signals having a phase offset of about 120° therebetween, i.e., a three-phase configuration. For example, phase 1 may be a reference phase having 0° phase shift, phase 2 vary from phase 1 by about 120°, and phase 3 may vary from phase 2 by about 120° and from phase 1 by about 240°. By this arrangement, a system operating in accordance with the present disclosure may operate in a balanced, or tri-polar, mode wherein a return electrode current (i.e. neutral current), is about zero because the total energy between the phases flows substantially among and between the electrodes of the instrument.

It is also contemplated that a system operating in accordance with the present disclosure may operate in an unbalanced state, which may cause current flow through a return electrode. For example, vaporization (a.k.a. "bubble steam") may form around an electrode altering the rate of energy flow thereat. In another instance, eschar may form at the operative site which may alter the impedance at one or more electrodes at the operative site, resulting in a change of energy transfer rate at the affected electrode(s). An unbalanced operating mode may also be achieved by altering the phase, amplitude, and/or frequency of at least one of the electrosurgical waveforms which may be useful, for example, for tailoring the shape or direction of the ablation region in accordance with therapeutic requirements. Additionally or alternatively, altering the phase, amplitude, and/or frequency of at least one of the electrosurgical waveforms may be useful to adapt the delivery of energy into tissue in response to conditions at the operative site, such as vaporization or eschar.

Also provided within the scope of the present disclosure is a control system for use with a polyphase electrosurgical generator which generates electrosurgical waveforms for application to tissue. At least one sensor module may be included that is configured to continually sense biometric parameters related to the operative site, including without limitation tissue impedance corresponding to the application of the electrosurgical waveforms to the tissue, and/or temperature of the operative site. The control system may include a controller configured to adjust the phase, amplitude, and/or frequency of one or more of the electrosurgical waveforms. A controller may be configured to adjust phase, amplitude, and/or frequency in response to a biometric parameter, such as, without limitation, tissue impedance, eschar formation, bubble steam formation, return pad current, and size and/or shape of the ablation region. Additionally or alternatively, a controller may be configured to adjust phase, amplitude, and/or frequency in response to a user input. For example, phase, amplitude or frequency may be independently adjusted by the user. In embodiments, the ability to select from predetermined combinations of phase, amplitude, frequency is provided.

In embodiments, the polyphase RF signals may be advantageously generated by digital synthesis. In embodiments, a digitized representation of a desired output waveform, which may be a sine wave, may be stored within the RF generator. The stored representation may be organized in lookup table form. The digitized representation may be converted into analog form via a digital-to-analog (D/A) converter. Each separately phased signal may be associated with a corresponding D/A converter. In embodiments, a single multiplexed D/A converter may be associated with each phased signal. The generator may be configured to include multiple pointers (i.e., an offset) to data points of the digitized waveform table corresponding to the desired phase offset between each polyphase signal. For example, a sine wave may be represented in a lookup table having 3,600 data points (i.e., samples), each point corresponding to the amplitude of a sine wave in 0.1° increments. Assuming a three-phase signal having 120° between phases, a first phase would correspond to an offset of 0 samples, a second phase would correspond to an offset of 1200 samples, and a third phase would correspond to an offset of 2400 samples. The stored data points are then processed by the D/A converters at the corresponding rate and offset to generate polyphase signals having the desired frequency and phase angle. The amplitude of each polyphase signal may be adjusted by, for example, digital scaling or a variable gain output amplifier. The phase angle of a selected signal may be adjusted by varying the table offset associated with that phase. Continuing with the present example, changing the table offset by a single location causes a phase change of 0.1°. Finer adjustments of phase may be achieved by, for example, interpolation of table values, or by providing a table having a greater number of data points.

The ability to control the return path of electrosurgical energy provided by the electrode cluster may be accomplished by altering the phase, amplitude, and/or frequency relationship between the waveforms. For example, in a simple monopolar configuration, RF energy will follow the path of least resistance (averaged over the three-dimensional volumetric pathway) between the electrode and return pad; there is no clear method to divert or alter the electrical current flow direction—that path is defined by the physiological parameters as the area is ablated. Similarly, in a bi-polar configuration, the current flows between the two electrodes and the surrounding normal tissue anatomy/physiology, as well as the ablation created, dictate the overall current pathway. Using a 3-phase multi-phase system, the device may be operated in a balanced mode (each electrode offset 120° in phase) to direct energy equally between the electrodes, in an unbalanced mode to deliver more current between specific electrodes and partially to the return pad, or in a single-phase mode where all the electrodes operate in the same phase (like a typical monopolar mode) which will direct the current only to the return pad. Adjusting the relative phases and amplitudes of the multi-phase system may provide a level of control to current flow paths and subsequent energy deposition.

In one envisioned embodiment, an altered phase relationship is fixed during activation of the electrodes, which may be useful to tailor the direction and shape of the ablation region in accordance with operative requirements. In another envisioned embodiment, the controller may be configured to adjust phase, amplitude, and/or frequency in accordance with predetermined time-varying contours. For example, amplitude modulation may be applied to each phase in succession to induce a quasi-rotating energy delivery pattern. In another example, the phases of two adjacent electrodes may be brought into or out of coherence over a period of time to alter the ablation area. This timed phase shift may be performed in a one-shot, multi-shot, or repeating manner. The shift pattern may be staggered or alternating, so that, for example, when the cluster electrodes are activated the phase difference between two electrode may continually vary from about 120° to about 0° and back to about 120° at a predetermined rate. In yet another embodiment, the phase, amplitude and frequency of each electrode is independently varied in according with predetermined patterns. Thus, by altering the relationships of phase, amplitude and frequency of each electrode with respect to the others, a variety of ablation effects may be achieved.

Other arrangements are contemplated within the scope of the present disclosure, for example, an embodiment having less than three, or more than three, independent RF signals. Such embodiments may have, for example, a generator capable of generating four RF signals having phase offsets of about 90° therebetween, or, as another example, a generator capable of generating six RF signals having phase offsets of about 60° therebetween.

In another aspect according to the present disclosure, a surgical instrument having a plurality of electrodes is disclosed. Each electrode may be operably coupled to a corresponding independent output of a polyphase RF generator. The electrodes may be arranged in any configuration, such as a triangle (i.e., delta) configuration or a linear configuration. In embodiments, the number of electrodes is a multiple of the number of independent RF signals provided by a polyphase RE generator. For example, a three-phase generator may be operably coupled to a surgical instrument having six electrodes configured in a hexagonal arrangement. Each RF signal, or phase, may be coupled to one or more electrodes. In embodiments, each phase may be coupled to respective electrodes of the cluster. As an example only, referring to each electrode by a letter A through F respectively around the perimeter defined by the hexagonal electrode array, phase 1 may be coupled to electrodes A and D, phase 2 to electrodes B and E, and phase 3 to C and F. In this manner, opposing electrodes of the array are commonly coupled to one phase provided by the generator. As another example, phase 1 may be coupled to electrodes A and B, phase 2 to electrodes C and D, and phase 3 to electrodes E and F. In yet another example, the phases may be coupled to an arbitrary combination electrodes.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
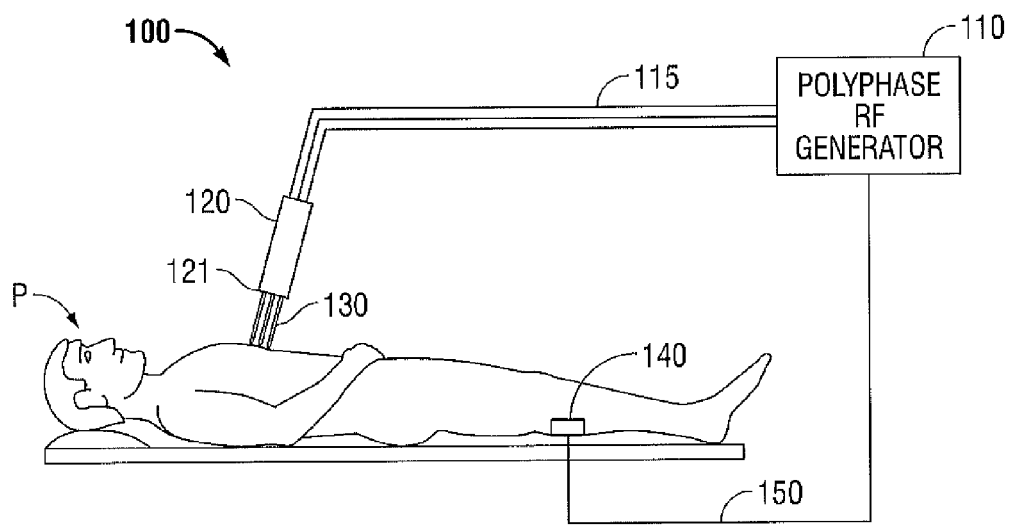
FIG. 1 is a schematic representation of a polyphase electrosurgical system in accordance with an embodiment of the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

With reference to FIG. 1, a polyphase electrosurgical system 100 in accordance with an embodiment of the present disclosure includes a polyphase RF generator 110 that is operably coupled to an electrosurgical instrument 120. A cluster electrode array 130 is provided at distal end 121 of electrosurgical instrument 120 for delivering electrosurgical energy to tissue of a patient P. Polyphase RF generator 110 may be operably coupled to an electrosurgical instrument 120 by a cable 115, which may be a multi-conductor cable. Polyphase electrosurgical system 100 may optionally be configured with at least one return electrode 140 to provide a return path for electrosurgical energy to polyphase RF generator 110 via conductor 150 operably coupled therebetween. As can be seen in FIG. 1, return electrode 140 may be positioned on the body of a patient at, for example, the leg, buttocks, or other medically-suitable location.

Figure 2:
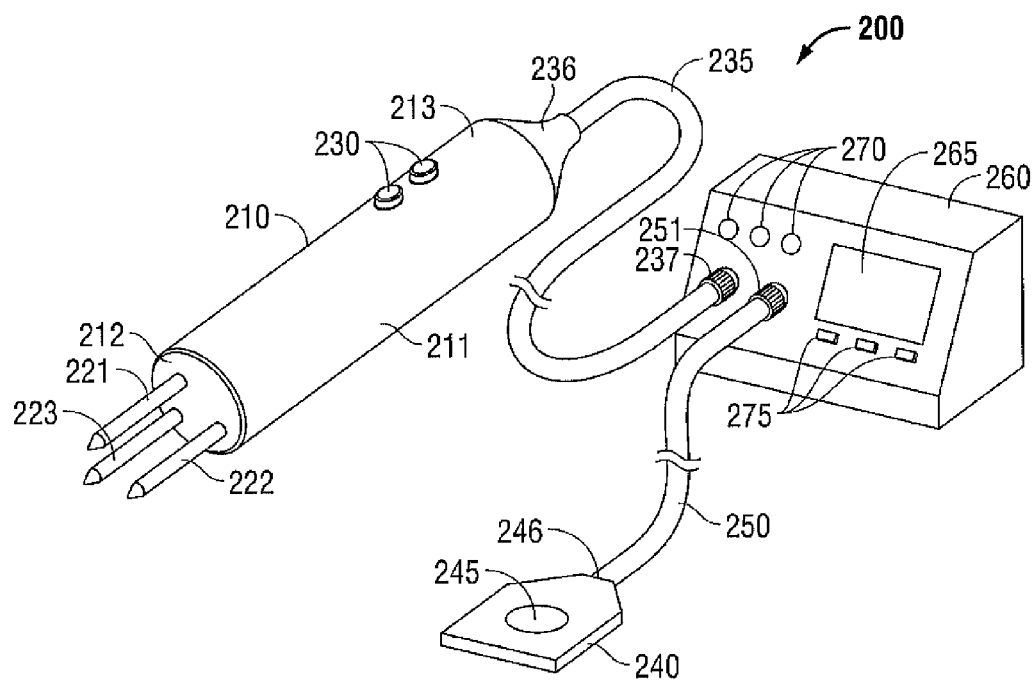
FIG. 2 is an illustration of a polyphase electrosurgical system in accordance with an embodiment of the present disclosure.

As shown in FIG. 2, aspects of a polyphase electrosurgical system in accordance with an embodiment of the present disclosure are shown as system 200 and include an electrosurgical instrument 210 having a housing 211 adapted for use by a user for performing open, percutaneous, endoscopic, or laparoscopic surgical procedures. The distal end 212 of instrument 210 may include electrodes 221, 222, and 223 that may be operably and/or independently coupled to separate sources of electrosurgical energy provided by polyphase electrosurgical generator 260. Instrument 210 may additionally include at least one user interface element 230, which may be used to facilitate control of the generator 260. For example, user interface element 230 may be a momentary pushbutton (e.g., push-on/release-off), toggle pushbutton (e.g., push-on/push-off) or sequence pushbutton (e.g., for stepping through alternative selections). Additionally, or alternatively, user interface element 230 may be a slide switch or continuously variable control, such as a potentiometer.

Instrument 210 may be operably coupled to polyphase generator 260 by a cable 235. In some embodiments, cable 235 may be detachably coupled to the instrument 210. Additionally, or alternatively, cable 235 may be detachably coupled to polyphase generator 260 via connector 237. A strain relief 236 may be included at the proximal end 213 of instrument 210.

Optionally, a return electrode pad 240 having a return electrode 245 incorporated therewith may be provided. Return electrode pad 240 may be operably coupled to polyphase generator 260 by a cable 250. In some embodiments, cable 250 may be detachably coupled to the instrument 210 and, additionally or alternatively, cable 250 may be detachably coupled to polyphase generator 260 via connector 251. Return electrode pad 240 may additionally include a connector 246 configured to couple cable 250 thereto.

Polyphase generator 260 may include at least one user input element 270, 275 and display element 265 to facilitate user interaction with the system. Display element 265 may be any suitable display device, including without limitation an LED display, an LCD display, a graphics display (e.g., flat panel), or an electromechanical indicator.

Figure 3:
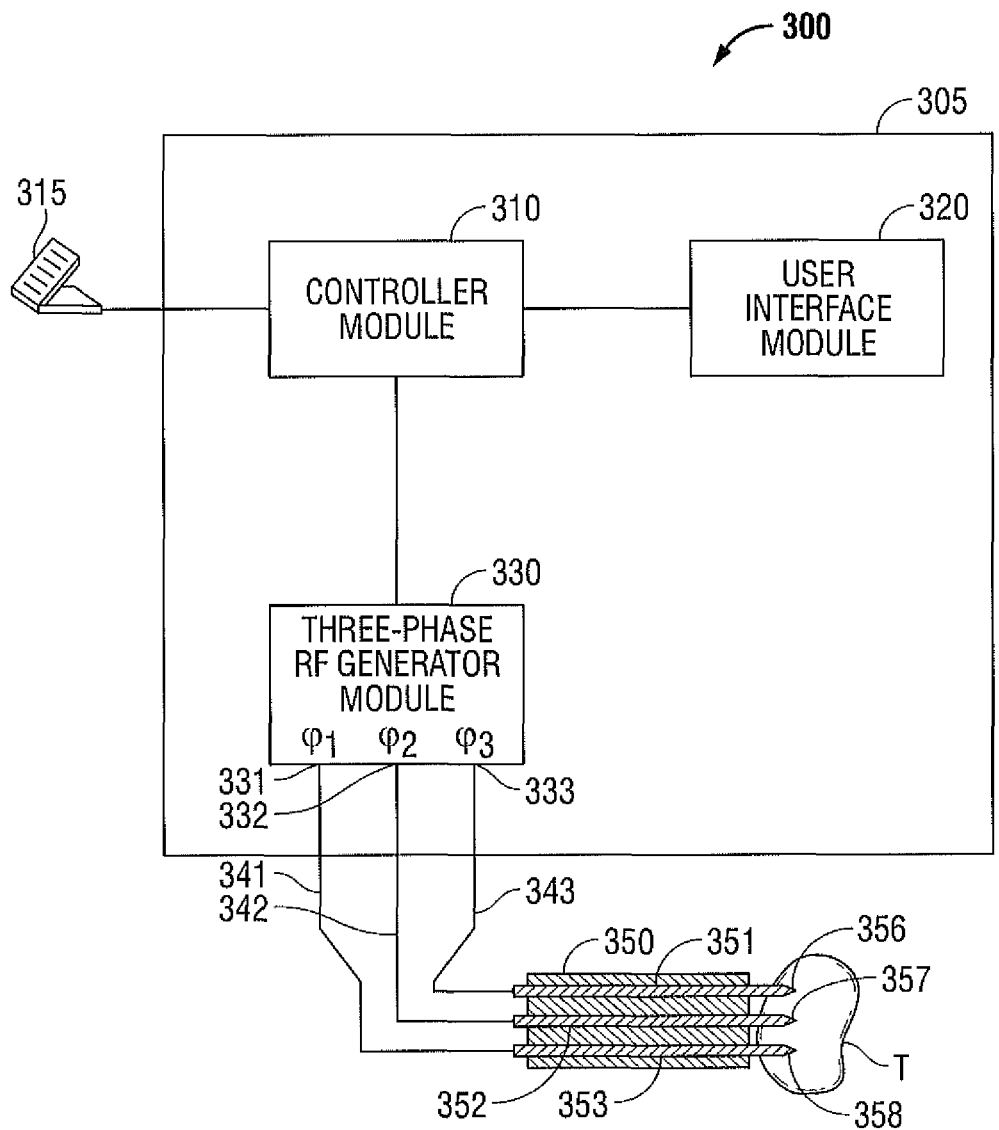
FIG. 3 is a block diagram of a polyphase electrosurgical system in accordance with an embodiment of the present disclosure.

In FIG. 3 there is illustrated a block diagram of a polyphase electrosurgical generator system 300 in accordance with an embodiment of the present disclosure. The system 300 includes a controller module 310 that is operably coupled to a three-phase generator module 330. Additionally, controller module 310 may be operably coupled to a user interface module 320 and/or an activation control, such as a footswitch 315. The controller 310, user interface module 320, and/or generator module 330 may conveniently be arranged in a common housing 305. Generator module 330 provides three RF outputs 331, 332, and 333, corresponding to phase 1, phase 2, and phase 3, respectively, of a polyphase electrosurgical signal. Each RF output 331, 332, and 333 may be operably coupled to electrodes 351, 352, and 353 by conductors 341, 342, and 343, respectively. Electrodes 351, 352, and 353 are disposed within an instrument housing 350 configured to position electrode tips 356, 357, and 358, at or adjacent to the distal end thereof. Instrument housing 350 may be constructed from materials that may include electrically non-conductive material, and may by be configured to electrically insulate electrodes 351, 352, and 353 from each other and from non-targeted tissue.

In use, controller module 310 may receive a user input from user interface module 320. For example, a user may select an amplitude, frequency, and/or phase relationship characterizing the desired electrosurgical signal. In some embodiments, a user may select a static electrosurgical signal, e.g., one characterized by a continuous steady-state delivery of energy. In other embodiments, the user may select a dynamically-changing signal, wherein at least one signal parameter changes on a temporal basis, for example without limitation, periodic modulation (e.g., pulse width modulation) and aperiodic modulation (e.g., altering a parameter in a predetermined or arbitrary manner over time).

Controller module 310 may additionally receive an activation signal from an activation control, such as a footswitch 315 or an activation control included with the instrument housing 350 (not explicitly shown). Upon receipt of an activation signal, controller module causes generator module 330 to begin outputting a polyphase RF signal at output 331, 332, and 333. The polyphase energy is conducted via conductors 341, 342, and 343 to electrodes 351, 352, and 353 for performing an electrosurgical procedure, such as ablation, on tissue T.

Figure 4:
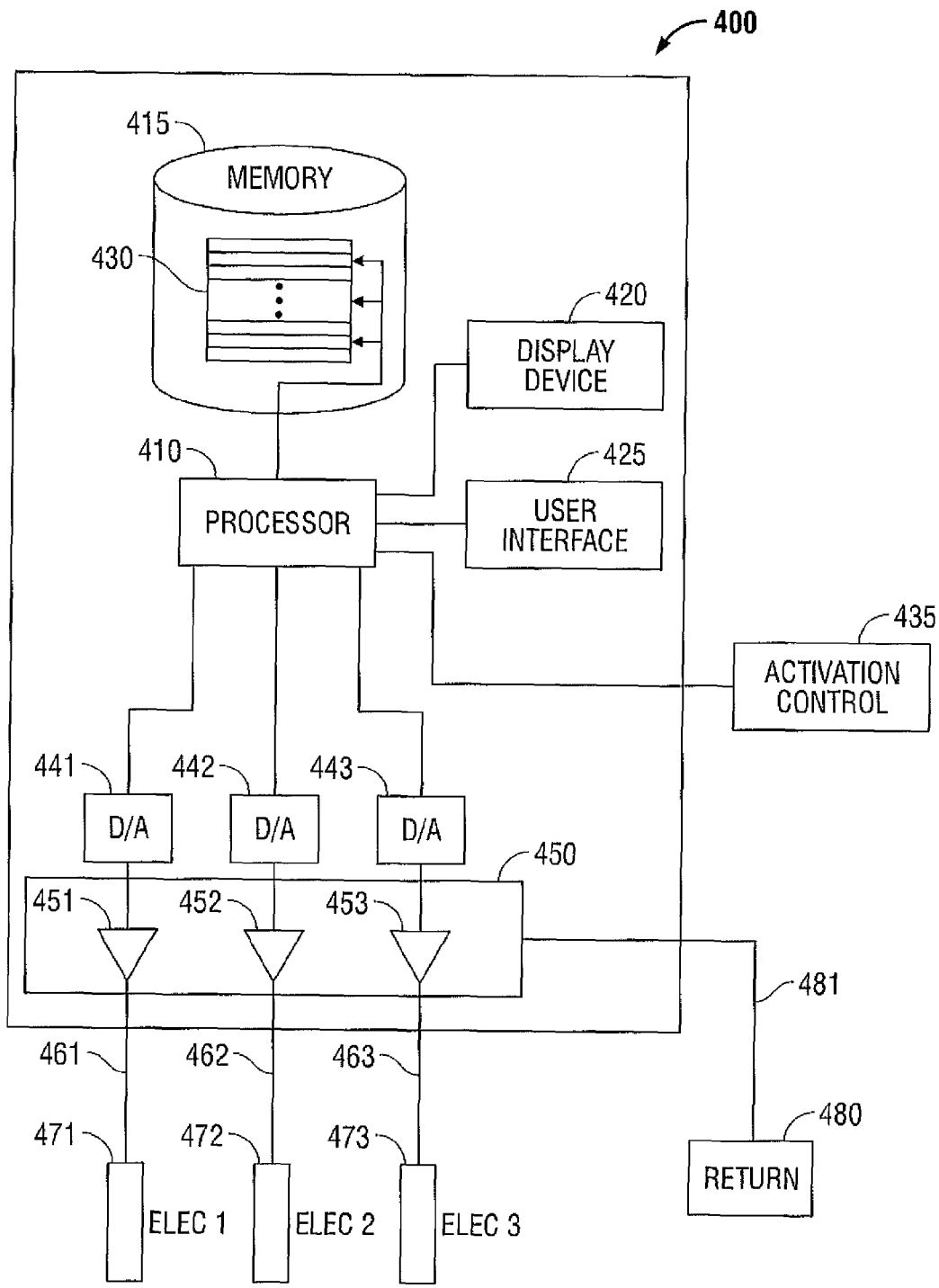
FIG. 4 is a block diagram of an example embodiment of a polyphase electrosurgical generator configured to digitally synthesize radiofrequency signals.

Shown in greater detail in FIG. 4, embodiments of the disclosed polyphase electrosurgical system are envisioned and are illustrated as system 400 that includes a processor 410 that is operably coupled to at least one storage device 415. The storage device may be of any type of suitable storage device, including without limitation fixed and/or removable solid state memory devices (such as dynamic RAM, flash memory, or read-only memory), or disk drives (i.e., magnetic, magneto-optical, or optical drives). Storage device 415 may contain a waveform table 430 that includes a digitized waveform representation, and may contain a set of programmable instructions configured for execution by processor 410.

Processor 410 is operably coupled to digital-to-analog (D/A) converters 441, 442, and 443 for converting a digital representation of a waveform into analog form. The outputs of D/A converters 441, 442, and 443 are operably coupled to output stages 451, 452, and 453, which collectively may form an energy module 450. Output stages 451 et seq. may be an amplifier for amplifying the output of D/A converters 441 et seq. to the power level required for electrosurgical procedures. Output stages 451 may include a low-pass filter. The gain of output stages 451 et seq. may be controlled by processor 410, by, for example without limitation, direct control of the output stage 451 et seq. by processor 410 via a control signal (not explicitly shown), or by scaling of the digital signal by the processor 410 prior to D/A conversion. Outputs of the output stages 451 et seq. are operably coupled to electrodes 471, 472, and 473 via conductors 461, 462, and 463 for delivering electrosurgical energy to the operative site. A return electrode 480 and corresponding return conductor 481 may be operably coupled to energy module 450.

Continuing with respect to FIG. 4, processor 410 may be operably coupled to a display device 420, a user interface 425, and at least one activation control 435 that may be, for example, a footswitch or a handswitch. Processor 410 may be configured to perform a set of programmable instructions for receiving inputs from user interface 425 and/or activation control 435, and for causing operational information to be displayed on display device 420. In response to inputs received from user interface 425 and/or activation control 435, processor 410 may be configured to read waveform data from waveform table 430 and cause the waveform data to be converted into analog form by D/A converters 441 et seq. The maimer in which data is read and/or caused to be converted into analog form is dependent upon the desired phase, amplitude and frequency relationships among and between the individual polyphase signals. For example, in an embodiment that provides a balanced three-phase polyphase signal, processor 410 may retrieve waveform data from waveform table 430 from three separate table locations. The offset between the separate table locations from which waveform data is retrieved may be the number of waveform samples corresponding to the desired phase difference, which, in the present example, is 120°. The phase difference among and between the individuals may thus be tailored by varying this offset.

Advantageously, the rate at which waveform samples are read from waveform table 430 and consequently converted to analog form is in direct proportion to the desired frequency of the polyphase signal and the number of samples that represent a single period of the waveform. For example, assume a 500 kHz signal is desired, and the waveform table 430 contains 120 samples that collectively represent a single period of the waveform. Since the period of a waveform is expressed as the reciprocal of the frequency, i.e., $p=1/f$, the period of a 500 kHz signal is 2 µs. Therefore, to generate a 500 kHz signal, the 120 samples representing a single period of the electrosurgical polyphase signal must be read and converted in a 2 µs time interval, which correspond to a rate of 16.7 ns per sample, or a sample frequency of 60 mHz.

The frequency of one or more individual polyphase signal may be adjusted by altering the rate at which waveform data is delivered to, and converted by, a D/A converter 441 et seq.

In some embodiments, the phase and amplitude relationships among and between the polyphase signals may be adjusted by, for example, processor 410 and/or energy module 450 to achieve a target return electrode 480 current. In some embodiments, a target return electrode current may be a minimal or nearly zero current. For example, a software algorithm (not explicitly shown) adapted to be executed by processor 410 receives an input corresponding to the return electrode 480 current. In response thereto, the algorithm may alter one or more of the phase and/or amplitude of a polyphase signal to minimize or nearly eliminate the return electrode 480 current.

Figure 5:
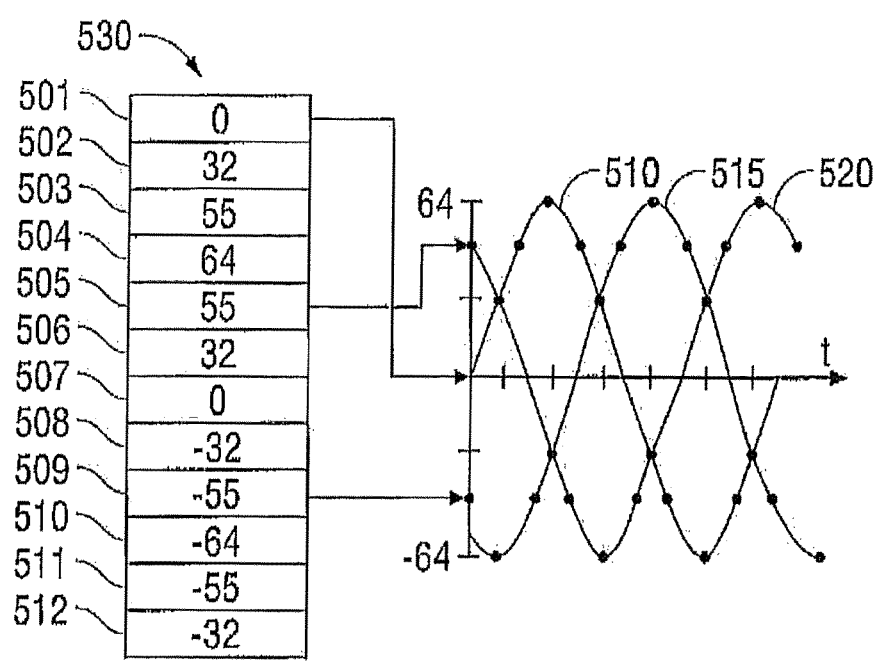
FIG. 5 is an example illustration of the relationship between a waveform table and polyphase signals generated by a polyphase electrosurgical system in accordance with the present disclosure.

The relationship between waveform data and polyphase signals is illustrated by example in FIG. 5 Waveform table 530 includes waveform data representing one period of a sine wave having twelve samples 501-512, and having maximum and minimum values scaled to +64 and −64 units, respectively. Phases 1, 2, and 3 of the polyphase signal are represented at 510, 515, and 520, respectively. Since twelve samples are shown in waveform table 530, it follows that the phase difference between each sample represents a phase shift of 30 degrees (360/12=30). Thus, in the present example, in order to generate polyphase signals having a phase difference of 120°, an offset of 4 samples between phases is indicated (120/30=4). Accordingly, phase 1 is generated by D/A converter 441 from samples beginning at sample 501, phase 2 is generated by D/A converter 442 from samples initially indexed at 505, and phase 3 is generated by D/A converter 443 from samples indexed beginning at 509. Waveform table 530 may be organized as a circular table, that is, after the final sample is reached, an index "wraps" back to the beginning of the table, i.e., sample 501. In this manner a continuous waveform may be generated.

In some embodiments, the respective phase difference between individual polyphase signals may be altered by altering the table offset accordingly. In some embodiments, table 530 may include greater or fewer samples, which may be scaled in any suitable manner, to correspond with, for example, the desired minimum phase angle resolution, or the amplitude resolution of D/A converter 441 et seq.

Figure 6A:
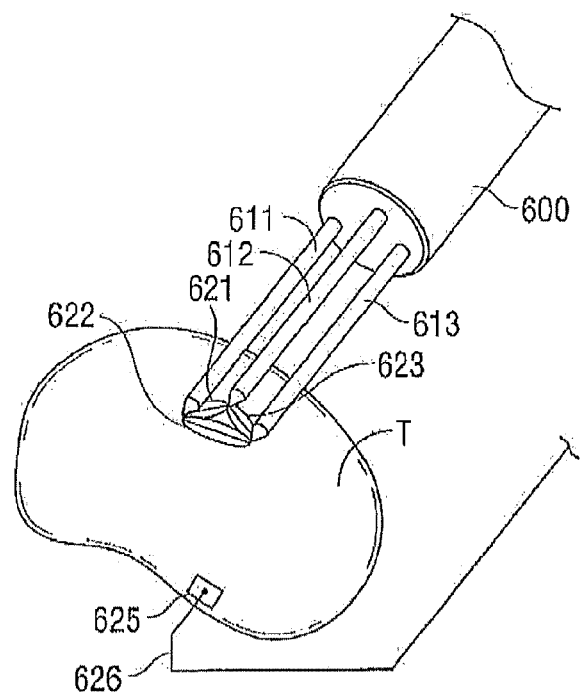
FIG. 6A is an example oblique view of an electrode cluster in accordance with the present disclosure illustrating balanced electric field lines between electrodes.
Figure 6B:
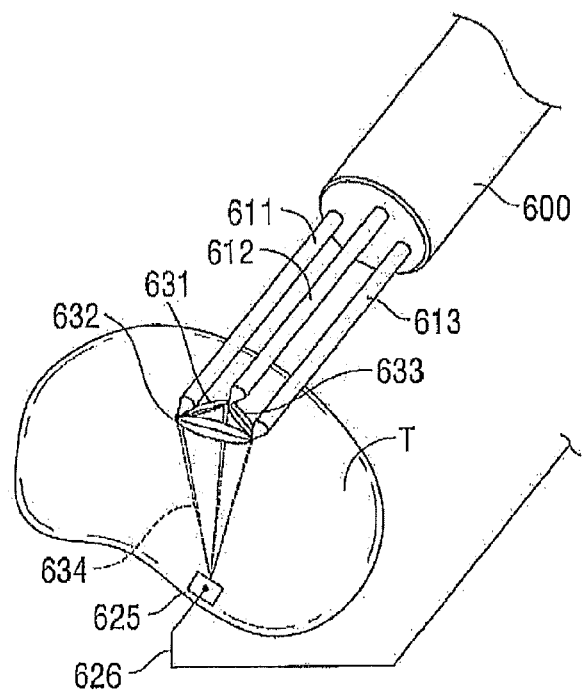
FIG. 6B is an example oblique view of an electrode cluster in accordance with the present disclosure illustrating unbalanced electric field lines between electrodes.

Turning now to FIGS. 6A and 6B, example embodiments in accordance with the present disclosure are presented wherein electric field lines representative of current flow are illustrated. As illustrated in FIGS. 6A and 6B return electrode 625 may be coupled to polyphase RF generator (not shown) via conductor 626. FIG. 6A depicts a polyphase electrosurgical probe 600 having a three-phase electrode cluster that includes electrodes 611, 612, and 613 that are shown delivering polyphase electrosurgical energy to tissue T in a balanced mode. As can be seen by representative current flow lines 621, 622, and 623, in a balanced mode energy flows among and between three-phase electrode cluster formed by electrodes 611, 612, and 613, while negligible or no current flow exists between the three-phase electrode cluster and return electrode 625. In FIG. 6B, the polyphase electrosurgical probe 600 is shown operating in an unbalanced mode, wherein energy flows among and between the three-phase electrode cluster as shown by representative current flow lines 631, 632, and 633 and between the electrode cluster and return electrode 625 as shown by representative current flow lines 634.

Figure 7A:
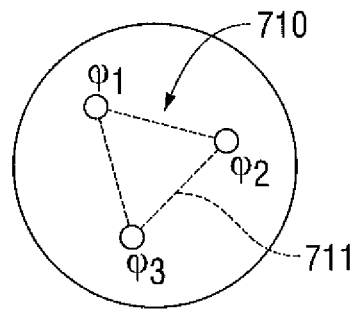
FIG. 7A is an example diagram showing an end view of an electrode configuration of a three-phase electrosurgical system having three electrodes in accordance with the present disclosure.
Figure 7B:
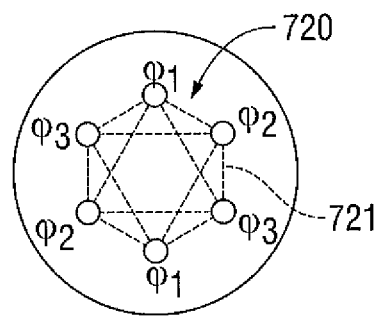
FIG. 7B is an example diagram showing an end view of an electrode configuration of a three-phase electrosurgical system having six electrodes in accordance with the present disclosure.
Figure 7C:
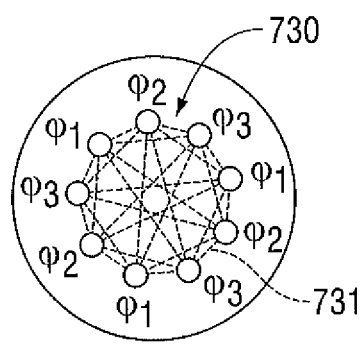
FIG. 7C is an example diagram showing an end view of an electrode configuration of a three-phase electrosurgical system having nine electrodes in accordance with the present disclosure.
Figure 7D:
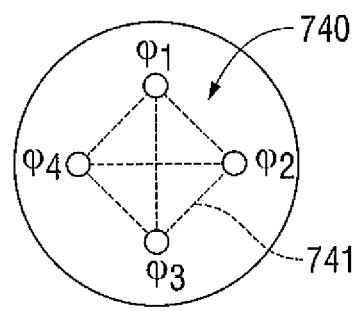
FIG. 7D is an example diagram showing an end view of an electrode configuration of a four-phase electrosurgical system having four electrodes in accordance with the present disclosure.
Figure 7E:
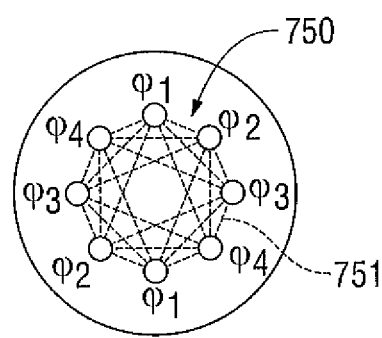
FIG. 7E is an example diagram showing an end view of an electrode configuration of a four-phase electrosurgical system having eight electrodes in accordance with the present disclosure.
Figure 7F:
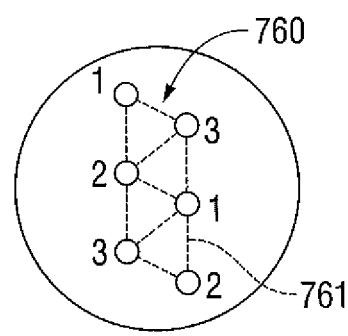
FIG. 7F is an example diagram showing an end view of a lattice electrode configuration of a three-phase electrosurgical system having six electrodes in accordance with the present disclosure.

In FIGS. 7A-7F, various illustrative arrangements of cluster electrodes and attendant current paths are shown. As can be seen in FIG. 7A, a polyphase electrosurgical system accordance with the present disclosure having a three-phase topology may have a cluster electrode array that includes a triangular or delta electrode configuration 710. In FIGS. 7B and 7C, an electrode configuration of a three-phase electrosurgical system having six electrodes 720 and nine electrodes 730, respectively, is shown. In FIGS. 7D and 7E, there is shown an exemplary configuration of a four-phase electrosurgical system having four electrodes 740 and eight electrodes 750, respectively, in accordance with the present disclosure. Other arrangements are contemplated and within the scope of the present disclosure, for example, as seen in the three-phase embodiment of FIG. 7F, a polyphase cluster electrode 760 may be configured in a linear or lattice-type arrangement. In each of FIGS. 7A, 7B, 7C, 7D, 7E, and 7F, the current paths between electrodes operating in a substantially balanced mode are depicted illustratively by 711, 721, 731, 741, 751, and 761, respectively. In embodiments, the phase relationship among and between multiple electrodes may be arbitrarily configured or patterned to tailor energy delivery patterns to achieve a particular ablation region shape.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A polyphase electrosurgical system, comprising:
   a storage device configured to store digitized waveform data;
   an energy module including three digital to analog converters and three amplifiers, each digital to analog converter configured to receive the digitized waveform data, convert the digitized waveform data to a respective radiofrequency signal, and deliver the respective radiofrequency signal to a respective amplifier of the three amplifiers, wherein:
   each respective radiofrequency signal has a phase offset relative to the other radiofrequency signals,
   each of the three amplifiers amplifies the respective radiofrequency signal and provides the respective radiofrequency signal to a respective output of the energy module, and
   the energy module is configured to adjust a frequency of each of the radiofrequency signals by altering a rate at which the digitized waveform data is converted by the digital to analog converters;
   an electrosurgical instrument having a housing and three distinct active electrodes extending externally from a distal end of the housing and disposed in spaced relation relative to each other, each distinct active electrode operably coupled to one of the respective outputs of the energy module, wherein each of the respective outputs is configured to deliver one of the provided respective radiofrequency signals to the respective distinct active electrode, each of the three distinct active electrodes defining an elongate shaft having a tapered distal tip configured to penetrate tissue;
   a tissue impedance sensor operatively coupled to at least one of the three distinct active electrodes and in communication with the energy module, the energy module configured to adjust the rate at which the digitized waveform data is converted by the digital to analog converters in response to a signal from the tissue impedance sensor;
   a return electrode operably coupled to the energy module and disposed in spaced relation to the electrosurgical instrument; and
   an actuator operably coupled to the energy module for activating the energy module.

2. The polyphase electrosurgical system of claim 1, wherein the phase offset is selected from the group consisting of about 120 degrees, about 90 degrees, and in the range of about 1 degree to about 180 degrees.

3. The polyphase electrosurgical system of claim 1, further comprising:
   a set of programmable instructions stored in the storage device for generating the radiofrequency signals; and
   a processor operably coupled to the storage device, the processor configured to execute the set of programmable instructions.

4. The polyphase electrosurgical system of claim 3, wherein the digitized waveform data is organized in a table, the table including:
   a first data point corresponding to a phase of a first sample radiofrequency signal; and
   a second data point corresponding to a phase of a second sample radiofrequency signal.

5. The polyphase electrosurgical system of claim 3, wherein the set of programmable instructions is configured to vary an amplitude of at least one of the radiofrequency signals.

6. The polyphase electrosurgical system of claim 3, wherein the set of programmable instructions is configured to vary a frequency of at least one of the radiofrequency signals.

7. The polyphase electrosurgical system of claim 3, further comprising a display module operably coupled to the processor for displaying operational parameters of the energy module.

8. The polyphase electrosurgical system of claim 1, wherein the actuator is selected from the group consisting of a handswitch and a footswitch.

9. The polyphase electrosurgical system of claim 1, wherein the energy module is configured to adjust at least one of the phase offset or an amplitude of at least one of the respective radiofrequency signals to minimize a target return electrode current.

10. The polyphase electrosurgical system of claim 1, wherein the distal end of the housing defines a planar surface perpendicular to a longitudinal axis defined by the housing and the three distinct active electrodes extend from the planar surface.

11. The polyphase electrosurgical system of claim 1, wherein the energy module is configured to:
adjust the frequency of each of the radiofrequency signals by altering a rate at which the digitized waveform data is delivered to the digital to analog
converters.

12. A polyphase electrosurgical system, comprising:
a storage device configured to store digitized waveform data;
an energy module including three digital to analog converters and three amplifiers, each digital to analog converter configured to receive the digitized waveform data, convert the digitized waveform data to a respective radiofrequency signal, and deliver the respective radiofrequency signal to a respective amplifier of the three amplifiers, wherein:
each respective radiofrequency signal has a phase offset relative to the other radiofrequency signals,
each of the three amplifiers amplifies the respective radiofrequency signal and provides the respective radiofrequency signal to a respective output of the energy module, and
the energy module is configured to adjust a frequency of each of the radiofrequency signals by altering a rate at which the digitized waveform data is converted by the digital to analog converters;
an electrosurgical instrument having a housing and three distinct active electrodes extending externally from a distal end of the housing and disposed in spaced relation relative to each other, each distinct active electrode operably coupled to one of the respective outputs of the energy module, wherein each of the respective outputs is capable of delivering the provided respective radiofrequency signals to the respective distinct active electrode, each of the three distinct active electrodes defining an elongate shaft having a tapered distal tip configured to penetrate tissue; and
a return electrode operably coupled to the energy module and disposed in spaced relation to the electrosurgical instrument.

13. The polyphase electrosurgical system of claim 12, wherein the energy module is configured to adjust at least one of the phase offset or an amplitude of at least one of the radiofrequency signals.

14. The polyphase electrosurgical system of claim 12, wherein the distal end of the housing defines a planar surface perpendicular to a longitudinal axis defined by the housing and the three distinct active electrodes extend from the planar surface.

15. The polyphase electrosurgical system of claim 12, wherein the energy module is configured to:
adjust the frequency of each of the radiofrequency signals by altering a rate at which the digitized waveform data is delivered to the digital to analog
converters.

16. A polyphase electrosurgical system, comprising:
a storage device configured to store digitized waveform data;
an energy module including a plurality of digital to analog converters and an amplifier corresponding to each of the plurality of digital to analog converters, each digital to analog converter configured to receive the digitized waveform data, convert the digitized waveform data to a respective radiofrequency signal, and deliver the respective radiofrequency signal to the corresponding amplifier, wherein:
each respective radiofrequency signal has a phase offset relative to the other radiofrequency signals,
each amplifier amplifies the respective radiofrequency signal and provides the respective radiofrequency signal to a respective output of the energy module, and
the energy module is configured to adjust a frequency of each of the radiofrequency signals by altering a rate at which the digitized waveform data is converted by the digital to analog converters; and
an electrosurgical instrument having a housing and three distinct active electrodes extending externally from a distal end of the housing and disposed in spaced relation relative to each other, each distinct active electrode operably coupled to one of the respective outputs of the energy module, wherein each of the respective outputs is capable of delivering one of the provided respective radiofrequency signals to the respective distinct active electrode, each of the three distinct active electrodes defining an elongate shaft having a tapered distal tip configured to penetrate tissue.

17. The polyphase electrosurgical system of claim 16, wherein the energy module is configured to:
adjust the frequency of each of the radiofrequency signals by altering a rate at which the digitized waveform data is delivered to the digital to analog
converters.

* * * * *